United States Patent
Modaressi et al.

(10) Patent No.: US 8,383,137 B2
(45) Date of Patent: Feb. 26, 2013

(54) AGRICULTURAL ADJUVANT COMPOSITIONS, HERBICIDE COMPOSITIONS, AND METHODS FOR USING SUCH COMPOSITIONS

(75) Inventors: Hedieh Modaressi, Princeton, NJ (US); Andrew Douglass, East Windsor, NJ (US)

(73) Assignee: Rhodia Operations, Aubervilliers (FR)

( * ) Notice: Subject to any disclaimer, the term of this patent is extended or adjusted under 35 U.S.C. 154(b) by 319 days.

(21) Appl. No.: 11/432,853

(22) Filed: May 12, 2006

(65) Prior Publication Data

US 2006/0264328 A1 Nov. 23, 2006

Related U.S. Application Data

(60) Provisional application No. 60/681,839, filed on May 17, 2005.

(51) Int. Cl.
*A61K 8/02* (2006.01)
(52) U.S. Cl. ......................................................... 424/401
(58) Field of Classification Search .................. None
See application file for complete search history.

(56) References Cited

U.S. PATENT DOCUMENTS

| | | | |
|---|---|---|---|
| 5,431,903 A * | 7/1995 | Majeti et al. ..................... | 424/52 |
| 5,580,856 A | 12/1996 | Prestrelski et al. | |
| 5,612,285 A * | 3/1997 | Arnold .......................... | 504/206 |
| 5,747,416 A | 5/1998 | Mcardle | |
| 5,945,377 A | 8/1999 | Penner et al. .................. | 504/116 |
| 6,364,926 B1 * | 4/2002 | Gryzik et al. .................. | 71/64.1 |
| 6,432,878 B1 | 8/2002 | Brigance | |
| 6,432,884 B1 | 8/2002 | Lachut | |
| 6,500,784 B1 * | 12/2002 | Mille et al. ..................... | 504/206 |
| 6,645,912 B1 * | 11/2003 | Mille et al. ..................... | 504/206 |
| 6,645,914 B1 | 11/2003 | Woznica et al. | |
| 6,770,594 B2 | 8/2004 | Bickers et al. | |
| 6,992,046 B2 | 1/2006 | Bramati et al. ................ | 504/206 |
| 2005/0130842 A1 | 6/2005 | Fleute-Schlachter et al. | |

FOREIGN PATENT DOCUMENTS

| | | |
|---|---|---|
| EP | 0 274 369 A1 | 7/1988 |
| EP | 0274369 A1 | 7/1988 |
| WO | 00/67571 A1 | 11/2000 |
| WO | 00/67573 A1 | 11/2000 |

OTHER PUBLICATIONS

Pratt et al., Substitutes for Ammonium sulfate as additives with Glyphosate and Glufosinate, Weed Technology, vol. 17:576-581, 2003.*

* cited by examiner

*Primary Examiner* — Robert T Crow
*Assistant Examiner* — Thor Nielsen
(74) *Attorney, Agent, or Firm* — Hunton & Williams, LLP

(57) ABSTRACT

Pesticide compositions that contain, based on 100 pbw of such composition, (a) greater than or equal to about 0.006 parts by weight of a betaine surfactant, (b) greater than or equal to about 0.02 parts by weight of a humectant selected from polyhydric alcohols, polysaccharide humectants, and mixtures thereof, and (c) an effective amount of a pesticide, exhibit reduced foaming and high efficacy.

9 Claims, No Drawings

AGRICULTURAL ADJUVANT COMPOSITIONS, HERBICIDE COMPOSITIONS, AND METHODS FOR USING SUCH COMPOSITIONS

This application claims the benefit of U.S. Provisional Application Ser. No. 60/681,839, filed May 17, 2005.

FIELD OF THE INVENTION

This invention relates to agricultural adjuvant compositions, pesticide compositions, and methods for using such compositions.

BACKGROUND OF THE INVENTION

Pesticide, such as herbicides, fungicides, insecticides, miticides, acaricides, and nematocides, are widely used in agricultural applications. As applied in the field, such compositions typically contain adjuvants, such as surfactants, to improve the handling properties of the compositions and improve the efficacy of such compositions.

There remains a continuing interest in pesticide compositions that exhibit good handling properties and high efficacy and in adjuvant compositions for use in such compositions.

SUMMARY OF THE INVENTION

In a first aspect, the present invention is directed to an adjuvant composition comprising, based on 100 parts by weight ("pbw") of the adjuvant composition:
(a) greater than or equal to about 0.1 pbw of a betaine surfactant, and
(b) greater than or equal to about 0.1 pbw of a humectant selected from polyhydric alcohols, polysaccharide humectants, and mixtures thereof.

In a second aspect, the present invention is directed to a pesticide composition, comprising, based on 100 pbw of such composition:
(a) greater than or equal to about 0.001 pbw of a betaine surfactant, and
(b) greater than or equal to about 0.005 pbw of a humectant selected from polyhydric alcohols, polysaccharide humectants, and mixtures thereof, and
(c) an effective amount of a pesticide.

In a third aspect, the present invention is directed to a method for treating a target plant, comprising applying to the plant a pesticide composition comprising, based on 100 pbw of such composition:
(a) greater than or equal to about 0.001 pbw a betaine surfactant, and
(b) greater than or equal to about 0.005 pbw of a humectant selected from polyhydric alcohols, polysaccharide humectants, and mixtures thereof, and
(c) an effective amount of a pesticide.

In a fourth aspect, the present invention is directed to an adjuvant composition comprising, based on 100 pbw of the adjuvant composition:
(a) from about 0.1 pbw to about 10 pbw of a betaine surfactant, and
(b) from about 5 pbw to about 50 pbw of ammonium sulfate.

DETAILED DESCRIPTION OF INVENTION AND PREFERRED EMBODIMENTS

Betaine surfactants are known compounds. In one embodiment, the betaine surfactant is a compound according to formula (I):

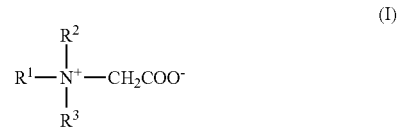

wherein:
$R^1$ is alkyl, alkenyl, or alkylamidoalkyl, and
$R^2$ and $R^3$ are each independently $(C_1-C_6)$alkyl or hydroxy $(C_1-C_6)$alkyl.

As used herein, "alkyl" means a saturated straight or branched chain hydrocarbon radical, typically a $(C_1-C_{30})$ saturated straight or branched chain hydrocarbon radical, such as for example, methyl, ethyl, n-propyl, iso-propyl, n-butyl, sec-butyl, t-butyl, pentyl, n-hexyl, cyclohexyl, octyl, decyl, dodecyl, tetradecyl, hexadecyl, octadecyl, eicosyl, behenyl, tricosyl.

As used herein, the term "alkenyl" means an unsaturated straight chain, branched chain, or cyclic hydrocarbon radical having at least one carbon-carbon double bond per radical, such as for example, propenyl, butenyl, octadecenyl.

As used herein, "alkylamidoalkyl" means a group according to formula (II):

wherein $R^4$ is alkyl or alkenyl, typically $(C_1-C_{30})$alkyl, and $R^5$ is an alkylenyl radical, typically $(C_1-C_6)$alkylenyl and includes, for example, dodeclyamidopropyl, tetradecylamidoethyl.

As used herein, "hydroxy$(C_1-C_6)$alkyl" means a hydroxyalkyl group having from 1 to 6 carbon atoms per group, such as for example hydroxymethyl, hydroxyethyl, hydroxypropyl, hydroxybutyl, hydroxypentyl, and hydroxyhexyl.

Suitable betaine surfactants include for example, $(C_{12}-C_{18})$alkydimethyl betaine, cocoamidopropyl betaine, and mixtures thereof.

In one embodiment, the betaine surfactant comprises a $(C_{12}-C_{14})$alkyldimethylbetaine.

Suitable polyhydric alcohols are compounds having at least two alcohol functional groups per molecule, including for example, diols, such as, ethylene glycol, propylene glycol, polyethylene glycol, and triols such as glycerol.

In one embodiment, the polyhydric alcohol comprises glycerol.

Suitable polysaccharide humectants include, for example, alkyl polysaccharides, pentoses, high fructose corn syrup, sorbitol and molasses.

In one embodiment, the polysaccharide humectant comprises high fructose corn syrup.

In one embodiment, the adjuvant composition comprises, based on 100 pbw of such composition, from about 1 to about 30 pbw, more typically from about 5 to about 25 pbw, and even more typically from about 5 to about 15 pbw, of the betaine surfactant, from about 1 to about 100 pbw, more typically from about 10 to about 90 pbw, and even more typically from about 10 to about 50 pbw, of the humectant, and from about 1 to about 70 pbw, more typically from about 15 to about 70 pbw, and even more typically from about 10 to about 35 pbw, of water.

In another embodiment, the adjuvant composition further comprises ammonium sulfate, typically from about 0.1 to about 50 pbw, more typically from about 5 to about 40 pbw, and even more typically from about 10 to about 35 pbw, of ammoniumsulfate, based on 100 pbw of such composition.

In an alternative embodiment, the adjuvant composition comprises, based on 100 pbw of such composition, from about 0.5 to about 10 pbw, more typically from about 1 to about 6 pbw, and even more typically from about 1.5 to about 6 pbw, of the betaine surfactant, from about 5 to about 40 pbw, more typically from about 10 to about 35 pbw, and even more typically from about 14 to about 34 pbw, of ammonium sulfate, and from about 50 to about 95 pbw, more typically from about 50 to about 85 pbw, and even more typically from about 52 to about 84 pbw, of water.

Suitable pesticides are biologically active compounds used to control agricultural pests and include, for example, herbicides, plant growth regulators, crop dessicants, fungicides, bacteriocides, bacteriostats, insecticides, miticides, nematocides, and insect repellants.

As used herein, the terminology "effective amount" in reference to the relative amount of a pesticide in a pesticide composition means the relative amount of pesticide that is effective to control a target pest, e.g., a target plant, fungus, or insect, when the pesticide composition is applied at a given application rate.

Suitable herbicides include, for example, triazine herbicides such as metribuzin, hexaxinone, or atrazine; sulfonylurea herbicides such as chlorsulfuron; uracils such as lenacil, bromacil, or terbacil; urea herbicides such as linuron, diuron, siduron, or neburon; acetanilide herbicides such as alachlor, or metolachlor; thiocarbamate herbicides such as benthiocarb, triallate; oxadiazolone herbicides such as oxadiazon; phenoxyacetic acids such as 2,4-D; diphenyl ether herbicides such as fluazifop, acifluorfen, bifenox, or oxyfluorfen; dinitro aniline herbicides such as trifluralin; organophosphonate herbicides such as glyphosate salts and esters; dihalobenzonitrile herbicides such as bromoxynil, or ioxynil, dipyridilium herbicides such as paraquat. Suitable fungicides include, for example, nitrilo oxime fungicides such as cymoxanil; imidazole fungicides such as benomyl, carbendazim, or thiophanate-methyl; triazole fungicides such as triadimefon; sulfenamide fungicides, such as captan; dithio-carbamate fungicides such as maneb, mancozeb, or thiram; chloronated aromatic fungicides such as chloroneb; dichloro aniline fungicides such as iprodione, strobilurin fungicides such as kresoximmethyl, trifloxystrobin or azoxystrobin; chlorothalonil; copper salt fungicides such as copper oxychloride; sulfur; phenylamides; and acylamino fungicides such as metalaxyl or mefenoxam. Suitable insecticides, include, for example, carbamate insecticides, such as methomyl, carbaryl, carbofuran, or aldicarb; organo thiophosphate insecticides such as EPN, isofenphos, isoxathion, chlorpyrifos, or chlormephos; organophosphate insecticides such as terbufos, monocrotophos, or terachlorvinphos; perchlorinated organic insecticides such as methoxychlor; synthetic pyrethroid insecticides such as fenvalerate, abamectin or emamectin benzoate, neonicotinoide insecticides such as thiamethoxam or imidacloprid; pyrethroid insecticides such as lambda-cyhalothrin, cypermethrin or bifenthrin, and oxadiazine insecticides such as indoxacarb, imidachlopryd, or fipronil. Suitable miticides include, for example, propynyl sulfite miticides such as propargite; triazapentadiene miticides such as amitraz; chlorinated aromatic miticides such as chlorobenzilate, or tetradifan; and dinitrophenol miticides such as binapacryl. Suitable nematicides include carbamate nematicides, such as oxamyl.

In one embodiment, the pesticide comprises one or more compounds selected from herbicides, plant growth regulators, crop dessicants, fungicides, bacteriocides, bacteriostats, insecticides, miticides, nematocides, insect repellants and mixtures thereof.

In one embodiment, the pesticide is selected from glufosinate, glyphosate, water soluble glufosinate salts, water soluble glyphosate salts, and mixtures thereof, including, for example sodium, potassium, isopropyl amine, or ammonium salts.

In one embodiment, the pesticide is selected from, the potassium salt of glyphosate, the sodium salt of glyphosate, the isopropyl amine salt of glyphosate, the ammonium salt of glyphosate, and mixtures thereof.

Pesticide compounds are, in general, referred herein to by the names assigned by the International Organization for Standardization (ISO). ISO common names may be cross-referenced to International Union of Pure and Applied Chemistry ("IUPAC") and Chemical Abstracts Service ("CAS") names through a number of sources such as, for example, the *Compendium of Pesticide Common Name.*

As used herein, the terminology "an herbicidally effective amount" in reference to the relative amount of herbicide in an herbicidal composition means the relative amount that is effective to control growth of a target plant when the herbicidal composition is applied to the target plant at a given application rate.

In one embodiment, the pesticide composition comprises, based on 100 pbw of the composition, from about 10 to about 90 pbw, more typically from about 30 to about 60 pbw of glyphosate acid.

In one embodiment, the pesticide composition comprises, based on 100 pbw of such composition, from about 0.001 to about 2 pbw, more typically from about 0.005 to about 1 pbw, and even more typically from about 0.003 to about 0.5 pbw, of the betaine surfactant, from about 0.01 pbw to about 2 pbw, more typically from about 0.005 to about 2 pbw, and even more typically from about 0.02 to about 1.6 pbw, of the humectant, from about 0.02 to about 8 pbw, more typically from about 0.1 to about 6 pbw, and even more typically from about 0.1 to about 5 pbw of a glyphosate herbicide acid equivalent, and from about 85 to about 99 pbw, more typically from about 90 to about 99 pbw, and even more typically from about 93 to about 99 pbw, of water.

In one embodiment, the pesticide composition further comprises a fertilizer. Such fertilizers can provide the primary nutrients of nitrogen, phosphorus and/or potassium such as urea ammonium nitrate (30-0-0), 10-34-0, secondary nutrients sulfur, calcium, magnesium such as ammonium thiosulfate 12-0-0-26S, micronutrient fertilizers containing zinc, iron, molybdenum, copper, boron, chlorine, magnesium, for example 0-0-1 3%-S; 3%-Zn; 2%-Fe; 2%-Mn and mixtures thereof. In this embodiment the pesticide comprises from about 85 to about 99 pbw, more typically from about 90 to about 99 pbw, and even more typically from about 93 to about 99 pbw of fertilizer and water mixture.

In another embodiment, the pesticide composition further comprises ammonium sulfate, typically from about 0.1 to about 2.5 pbw, more typically from about 0.3 to about 2.5 pbw, and even more typically from about 0.7 to about 2.5 pbw, of ammonium sulfate, based on 100 pbw of such composition.

The adjuvant and pesticide compositions of the present invention may each, optionally, further comprise one or more agronomically acceptable solvent. Suitable solvents include, for example, water, and organic solvents, such as for example, alkylated aromatic solvents, such as toluene or alkylated naphthalenes and mineral oil fractions, such as paraffinic hydrocarbons, vegetable oils, alkylated seed oils, dibasic esters.

In one embodiment, the compositions of the present invention may optionally further comprise one or more water conditioners, such as for example, chelating agents, such as ethylenediamine tetraacetic acid, complexing agents such as ammonium sulfate, and pH adjusting agents, such as citric acid, polyacrylic acid, antifoams and spreaders.

In one embodiment, the pesticide composition of the present invention comprises, based on 100 pbw of such composition, from about 0.1 to about 3 pbw, more typically from about 0.7 to about 2.5 pbw, of one or more water conditioners, typically ammonium sulfate.

The pesticide composition of the present invention may, optionally, further comprise, based on 100 pbw of the composition, (up to about one pbw of other ingredients), one or more other amphoteric surfactants, such as for example, alkylaminopropionate, in addition to the betaine surfactant, one or more anionic surfactants, such as phosphate esters, one or more cationic surfactant, such as amine oxides, one or more nonionic surfactants, such as fatty acid esters, glycerol esters, sorbitan esters, and ethoxylated sorbitan esters, ethoxylated aliphatic alcohols, ethoxylated aliphatic acids and ethoxylated aliphatic phenols, ethoxylated tristyrylphenols, ethoxypropoxy compounds and derivatives, one or more alkylpolyglycosides, one or more thickeners, such as polysaccharide thickeners, including xanthan gum, and polyacrylamide thickeners, as well as antifoams, spreaders, and drift control agents.

The herbicidal composition is applied to a target plant, typically to foliage of the target plant, to control growth of the target plant.

In one embodiment, the pesticide composition is spray applied to foliage of a target plant at a rate of from about 0.5 pint/acre to about 3 pint/acre, more typically from about 0.5 to about 2.5, still more typically from about 1 to about 2.25 pint/acre.

EXAMPLES 1-18

The adjuvant compositions of Examples 1-18 were aqueous solutions made by adding ingredients ($C_{12}$-$C_{14}$)alkyldimethyl betaine ("Betaine"), glycerin, and ammonium sulfate in the relative amounts set forth below in TABLE I to water and mixing.

The storage stability of the adjuvant compositions was evaluated visually. Storage was carried out under 5 different conditions and readings were taken at 3 time intervals. Thus, observations were made after storage at 25° C., 2° C., 45° C., −16° C. and freeze-thaw conditions for 24 hours, after storage at 25° C., 2° C., 45° C., −16° C. and freeze-thaw conditions for 1 week, and after storage at 25° C., 2° C., 45° C., −16° C. and freeze-thaw conditions for 3 weeks. Results of the stability evaluation are given below in TABLE I.

TABLE I

| | Ingredients (ppw/100 pbw) | | | Stability | | |
|---|---|---|---|---|---|---|
| EX # | Ammonium sulfate | Betaine (30% active) | Glycerin | 24 hr | 1 week | 3 weeks |
| 1 | 35 | 13 | 7 | Unstable | Unstable | Unstable |
| 2 | 34 | 20 | — | Unstable | Unstable | Unstable |
| 3 | 34 | 15 | — | Unstable | Unstable | Unstable |
| 4 | 34 | 10 | — | Unstable | Unstable | Unstable |
| 5 | 34 | 5 | — | Stable | stable | stable |
| 6 | 32 | 20 | — | Unstable | Unstable | Unstable |
| 7 | 32 | 20 | 6 | Unstable | Unstable | Unstable |
| 8 | 32 | 14 | 8.3 | Stable | stable | stable |
| 9 | 32 | 13 | 7 | Stable | stable | stable |
| 10 | 28 | 20 | — | Stable | stable | stable |
| 11 | 28 | 20 | 6 | Stable | stable | stable |
| 12 | 28 | 16 | — | Stable | stable | stable |
| 13 | 28 | 14 | 7 | Stable | stable | stable |
| 14 | 28 | 13 | 7 | Stable | stable | stable |
| 15 | 23 | 13.5 | — | Stable | stable | stable |
| 16 | 20 | 12 | — | Stable | stable | stable |
| 17 | 17 | 10 | — | Stable | stable | stable |
| 18 | 14 | 7 | — | Stable | stable | stable |

EXAMPLES 19 AND 20 AND COMPARATIVE EXAMPLES C1-C3

The compositions of Examples 19 and 20 and Comparative Examples C1-C8 were aqueous solutions made by diluting 2.4 g of an aqueous solution containing adjuvants in the relative amounts set forth below and containing 450 g/L of iso-propyl amine salt of glyphosate ("glyphosate IPA") with water to give 100 milliliters of the solution. The relative amounts of the adjuvants are given as percent by weight ("wt %") of the solution before dilution.

| Example # | Adjuvants |
|---|---|
| C1 | none (control) |
| C2 | 3 wt % ($C_{12}$-$C_{14}$)alkyldimethylbetaine |
| C3 | 10 wt % glycerin |
| C4 | 1.5 wt % ($C_{12}$-$C_{14}$)alkyldimethylbetaine |
| C5 | 5 wt % glycerin |
| C6 | 10 wt % tallow amine ethoxylate (15 moles EO) |
| C7 | 5 wt % tallow amine ethoxylate (15 moles EO) 5 wt % glycerin |
| C8 | 10 wt % high fructose corn syrup |
| 19 | 1.5 wt %($C_{12}$-$C_{14}$)alkyldimethylbetaine 2.5 wt % glycerin 2.5 wt % high fructose corn syrup |
| 20 | 1.5 wt %($C_{12}$-$C_{14}$)alkyldimethylbetaine 5 wt % glycerin |

The foam forming properties of the aqueous solutions of Examples 19 and 20 and Comparative Examples C1-C8 were tested according to Collaborative International Pesticides Analytical Council ("CIPAC") MT-47. Results for hard water (1100 ppm) are given below in Table II. Results for soft water (60 ppm) are given below in TABLE III.

TABLE II

| | Foam (mm) | | | |
|---|---|---|---|---|
| Example # | 0 | 10" | 30" | 60" |
| C1 | 5 | 3 | 1 | 0 |
| C2 | 28 | 24 | 23 | 20 |

TABLE II-continued

| | Foam (mm) | | | |
|---|---|---|---|---|
| Example # | 0 | 10" | 30" | 60" |
| C3 | 5 | 3.5 | 1 | 0 |
| C4 | 29 | 27 | 25 | 23 |
| C5 | 4 | 3 | 0 | 0 |
| C6 | 30 | 28 | 21 | 15 |
| C7 | 13 | 12 | 12 | 10 |
| C8 | 6 | 4 | 3 | 2 |
| 19 | 27 | 25 | 23 | 21 |
| 20 | 19 | 18 | 15 | 13 |

TABLE III

| | Foam (mm) | | | |
|---|---|---|---|---|
| Example # | 0 | 10" | 30" | 60" |
| C1 | 1 | 0 | 0 | 0 |
| C2 | 49 | 46 | 40 | 40 |
| C3 | 6 | 4 | 2.5 | 1 |
| C4 | 40 | 40 | 34 | 30 |
| C5 | 9 | 6 | 2 | 0 |
| C6 | 33 | 30 | 19 | 13 |
| C7 | 30 | 27 | 18 | 13 |
| C8 | 6 | 3 | 0 | 0 |
| 19 | 30 | 28 | 27 | 25 |
| 20 | 32 | 30 | 28 | 26 |

EXAMPLES 21 AND 22 AND COMPARATIVE EXAMPLES C9-C11

The compositions of Examples 21 and 22 and Comparative Examples C9-C11 were aqueous solutions made by the ingredients in the relative amounts set forth below to water and mixing:

| Example # | Ingredients |
|---|---|
| 21 | 37.4% acid equivalent ("a.e.") glyphosate IPA<br>1.5% ($C_{12}$-$C_{14}$)alkyldimethylbetaine<br>5% high fructose corn syrup |
| 22 | 37.5% a.e. glyphosate IPA<br>1.5% ($C_{12}$-$C_{14}$)alkyldimethylbetaine<br>5% glycerol |
| C9 | 37.8% a.e. glyphosate IPA<br>3% ($C_{12}$-$C_{14}$)alkyldimethylbetaine |
| C10 | WeatherMax (Monsanto) |
| C11 | water only |

WeatherMax is a commercial formulation of glyphosate.

The efficacy of the compositions in controlling plant growth was tested by applying the compositions to the following plant species:

Common Lambsquarter ("LQ")
Redroot Pigweed ("PW")
Common Purslane ("CP")
Velvetleaf ("VL")
Ivy Morning Glory ("MG")
Common Waterhemp ("WH")
Shattercane ("SC")
Giant Foxtail ("GF")
Barnyard Grass ("BG")

at a rate of 0.5 pint per acre and at a rate of 1.0 pint per acre. Results for the 0.5 pint per acre application rate at 7, 14 and 20 days post application are given below in sections IV-A, IV-B, and IV-C of TABLE IV as percent control of plant growth (on a scale from 0 percent control, indicating no effect on plant growth, to 100% control, indicating total prevention of plant growth). Results for the 1.0 pint per acre application rate are given below in section IV-D of TABLE IV as percent control of plant growth.

TABLE IV

| Ex# | LQ | PW | CP | VL | IMG | CC | WH | SC | GF | BG |
|---|---|---|---|---|---|---|---|---|---|---|
| IV-A: Percent Control of Plant Growth, 7 Days, 0.5 pint/acre | | | | | | | | | | |
| 21 | 42 | 45 | 40 | 30 | 25 | 60 | 45 | 55 | 62 | 43 |
| 22 | 47 | 43 | 38 | 22 | 18 | 60 | 45 | 58 | 63 | 42 |
| C9 | 58 | 50 | 48 | 25 | 20 | 62 | 47 | 69 | 48 | 28 |
| C10 | 58 | 53 | 43 | 22 | 25 | 63 | 4 | 48 | 38 | 50 |
| C11 | 0 | 0 | 0 | 0 | 0 | 0 | 0 | 0 | 0 | 0 |
| IV-B: Percent Control of Plant Growth, 14 Days, 0.5 pint/acre | | | | | | | | | | |
| 21 | 47 | 57 | 55 | 32 | 32 | 85 | 50 | — | 78 | 73 |
| 22 | 62 | 48 | 58 | 25 | 27 | 75 | 63 | 67 | 85 | 73 |
| C9 | 63 | 58 | 56 | 27 | 27 | 77 | 57 | 77 | 75 | 64 |
| C10 | 70 | 65 | 57 | 23 | 32 | 72 | 57 | 50 | 73 | 83 |
| C11 | 0 | 0 | 0 | 0 | 0 | 0 | 0 | 0 | 0 | 0 |
| IV-C: Percent Control of Plant Growth, 20 Days, 0.5 pint/acre | | | | | | | | | | |
| 21 | 65 | 70 | 57 | 38 | 37 | 90 | 60 | 73 | 95 | 85 |
| 22 | 77 | 67 | 75 | 38 | 30 | 85 | 70 | 78 | 97 | 83 |
| C9 | 80 | 63 | 74 | 35 | 30 | 82 | 65 | 80 | 85 | 78 |
| C10 | 80 | 73 | 75 | 37 | 37 | 80 | 70 | 72 | 88 | 90 |
| C11 | 0 | 0 | 0 | 0 | 0 | 0 | 0 | 0 | 0 | 0 |
| IV-D: Percent Control of Plant Growth, 7 Days, 1.0 pint/acre | | | | | | | | | | |
| 21 | 60 | 65 | 55 | 32 | 27 | 72 | 53 | 78 | 65 | 58 |
| 22 | 62 | 68 | 45 | 37 | 28 | 72 | 50 | 77 | 75 | 62 |
| C9 | 72 | 65 | 47 | 33 | 35 | 73 | 58 | 87 | 85 | 72 |
| C10 | 73 | 65 | 50 | 32 | 35 | 70 | 68 | 83 | 68 | 58 |
| C11 | 0 | 0 | 0 | 0 | 0 | 0 | 0 | 0 | 0 | 0 |

The invention claimed is:

1. An adjuvant composition for a pesticide consisting essentially of, based on 100 parts by weight of the adjuvant composition:

(a) greater than or equal to about 1 part by weight of betaine surfactant, (b) greater than or equal to about 1 part by weight of glycerol, and (c) optionally, one or more solvents, thickeners, antifoam agents, spreaders, drift control agents, water conditioners, or fertilizers.

2. The composition of claim 1, wherein the betaine surfactant is selected from ($C_{12}$-$C_{18}$)alkyldimethyl betaine, cocoamidopropyl betaine, and mixtures thereof.

3. The composition of claim 1, wherein the betaine surfactant comprises ($C_{12}$-$C_{18}$)alkyldimethyl betaine.

4. The adjuvant composition of claim 1, wherein the amount of surfactant is from 1 to about 30 parts by weight and the amount of glycerol is from about 10 to about 90 parts by weight.

5. The adjuvant composition of claim 1, wherein the amount of surfactant is from 5 to about 25 parts by weight and the amount of glycerol is from about 10 to about 90 parts by weight.

6. The adjuvant composition of claim 1, wherein said composition consists of, based on 100 parts by weight of the adjuvant composition:

(a) greater than or equal to about 1 part by weight of betaine surfactant, (b) greater than or equal to about 1 part by weight of glycerol, and (c) optionally, one or more solvents, thickeners, antifoam agents, spreaders or drift control agents, water conditioners, or fertilizers.

7. The composition of claim 6, wherein at least one of said one or more water conditioners comprises ammonium sulfate.

8. The composition of claim 1, wherein at least one of said one or more water conditioners comprises ammonium sulfate.

9. The composition of claim 8, wherein said composition comprises greater than 0.1 parts by weight of ammonium sulfate.

* * * * *